(12) United States Patent
Sato

(10) Patent No.: US 11,509,834 B2
(45) Date of Patent: Nov. 22, 2022

(54) IMAGE PROCESSING APPARATUS AND IMAGE PROCESSING METHOD

(71) Applicant: OLYMPUS CORPORATION, Tokyo (JP)

(72) Inventor: Tomoya Sato, Tokorozawa (JP)

(73) Assignee: OLYMPUS CORPORATION, Tokyo (JP)

( * ) Notice: Subject to any disclaimer, the term of this patent is extended or adjusted under 35 U.S.C. 154(b) by 251 days.

(21) Appl. No.: 16/909,362

(22) Filed: Jun. 23, 2020

(65) Prior Publication Data

US 2020/0322564 A1 Oct. 8, 2020

Related U.S. Application Data

(63) Continuation of application No. PCT/JP2018/041234, filed on Nov. 6, 2018.

(30) Foreign Application Priority Data

Dec. 26, 2017 (JP) .............................. JP2017-249132

(51) Int. Cl.
*H04N 5/58* (2006.01)
*A61B 1/00* (2006.01)
(Continued)

(52) U.S. Cl.
CPC ..... *H04N 5/2354* (2013.01); *A61B 1/000095* (2022.02); *A61B 1/045* (2013.01); *G02B 23/26* (2013.01); *H04N 5/58* (2013.01)

(58) Field of Classification Search
CPC .... H04N 5/58; H04N 5/2354; A61B 1/00009; A61B 1/045
See application file for complete search history.

(56) References Cited

U.S. PATENT DOCUMENTS

| 6,343,158 B1* | 1/2002 | Shiohara | .................. H04N 5/20 345/611 |
| 2009/0066787 A1* | 3/2009 | Yamazaki | .............. A61B 1/063 348/70 |

(Continued)

FOREIGN PATENT DOCUMENTS

| JP | S63-173182 A | 7/1988 |
| JP | 2000148987 A | * 5/2000 |

(Continued)

OTHER PUBLICATIONS

Sato, Kazuchika, Katagiri, Tetsuya, Kamon, Koichi, Serita, Yasuaki, Contrast Improvement for linear/log CMOS image sensor, Konica Minolta Technoloy report 2007, vol. 4 , pp. 82-87 (Year: 2007).*

(Continued)

*Primary Examiner* — Rowina J Cattungal
(74) *Attorney, Agent, or Firm* — Scully, Scott, Murphy & Presser, P.C.

(57) ABSTRACT

An image processing apparatus includes: a dividing processing circuit configured to divide an imaging signal that is obtained by capturing an image of inside of a subject into a first base component and a detail component, the first base component corresponding to an illumination component of an object, the detail component corresponding to a reflectance component of the object; a color enhancement processing circuit configured to generate a second base component by performing a color enhancement process on the first base component, the color enhancement process being a process of increasing color gradation of a mucosa color in a predetermined color space; and a synthesizing circuit configured to synthesize the second base component and the detail component to output a synthesized signal.

10 Claims, 10 Drawing Sheets

(51) Int. Cl.
  *H04N 5/235* (2006.01)
  *A61B 1/045* (2006.01)
  *G02B 23/26* (2006.01)

(56) References Cited

U.S. PATENT DOCUMENTS

| | | | |
|---|---|---|---|
| 2012/0106867 A1* | 5/2012 | Yamada | G06T 5/008 |
| | | | 382/274 |
| 2015/0379698 A1 | 12/2015 | Kuramoto et al. | |
| 2017/0000406 A1* | 1/2017 | Schnidar | A61B 5/0077 |
| 2019/0058844 A1 | 2/2019 | Sato | |

FOREIGN PATENT DOCUMENTS

| | | |
|---|---|---|
| JP | 2012-213552 A | 11/2012 |
| JP | 2016-010506 A | 1/2016 |
| JP | 2017-202241 A | 11/2017 |
| WO | 2015/025620 A1 | 2/2015 |
| WO | 2017/022324 A1 | 2/2017 |
| WO | 2017/203866 A1 | 11/2017 |
| WO | 2017/203996 A1 | 11/2017 |

OTHER PUBLICATIONS

International Search Report dated Jan. 15, 2019 received in PCT/JP2018/041234.
Japanese Office Action dated Aug. 2, 2022 received in 2021-150001.

* cited by examiner

IMAGE PROCESSING APPARATUS AND IMAGE PROCESSING METHOD

CROSS-REFERENCE TO RELATED APPLICATION

This application is a continuation of PCT International Application No. PCT/JP2018/041234 filed on Nov. 6, 2018, which designates the United States, incorporated herein by reference, and which claims the benefit of priority from Japanese Patent Application No. 2017-249132, filed on Dec. 26, 2017, incorporated herein by reference.

BACKGROUND

1. Technical Field

The present disclosure relates to an image processing apparatus and an image processing method that perform a color enhancement process of increasing color gradation in a predetermined color space with respect to an imaging signal that is obtained by capturing an image of inside of a subject.

2. Related Art

In the related art, a technology for suppressing degradation of contrast of an image and adjusting brightness in an endoscope has been known (for example, see International Publication No. WO 2017/022324). In this technology, a video signal input from the endoscope is divided into a first signal, which includes a contrast component signal, and a second signal other than the contrast component signal, a brightness adjustment process is performed on the second signal, and the first signal and the second signal are synthesized again.

SUMMARY

In some embodiments, an image processing apparatus includes: a dividing processing circuit configured to divide an imaging signal that is obtained by capturing an image of inside of a subject into a first base component and a detail component, the first base component corresponding to an illumination component of an object, the detail component corresponding to a reflectance component of the object; a color enhancement processing circuit configured to generate a second base component by performing a color enhancement process on the first base component, the color enhancement process being a process of increasing color gradation of a mucosa color in a predetermined color space; and a synthesizing circuit configured to synthesize the second base component and the detail component to output a synthesized signal. The color enhancement processing circuit is configured to convert the first base component including an R component, a G component, and a B component into an L component, an a component, and a b component in an Lab color space, perform an enhancement process on the a component for extending a color distribution range, perform an enhancement process on the b component for extending a color distribution range, and convert the a component subjected to the enhancement process, the b component subjected to the enhancement process, and the L component into the second base component including an R component, a G component, and a B component.

In some embodiments, an image processing apparatus includes: a dividing processing circuit configured to divide an imaging signal that is obtained by capturing an image of inside of a subject into a base component and a detail component, the base component corresponding to an illumination component of an object, the detail component corresponding to a reflectance component of the object; a synthesizing circuit configured to perform a predetermined enhancement process on at least one of the base component and the detail component, and subsequently synthesize the base component and the detail component to output a first synthesized signal; and a color enhancement processing circuit configured to output a second synthesized signal that is obtained by performing a color enhancement process on the first synthesized signal output from the synthesizing circuit, the color enhancement process being a process of increasing color gradation of a mucosa color in a predetermined color space. The color enhancement processing circuit is configured to convert the first synthesized signal including an R component, a G component, and a B component into an L component, an a component, and a b component in an Lab color space, perform an enhancement process on the a component for extending a color distribution range, perform an enhancement process on the b component for extending a color distribution range, and convert the a component subjected to the enhancement process, the b component subjected to the enhancement process, and the L component into the second synthesized signal including an R component, a G component, and a B component.

In some embodiments, an image processing method includes: dividing an imaging signal that is obtained by capturing an image of inside of a subject into a first base component and a detail component, the first base component corresponding to an illumination component of an object, the detail component corresponding to a reflectance component of the object; generating a second base component by performing a color enhancement process on the first base component, the color enhancement process being a process of increasing color gradation of a mucosa color in a predetermined color space; and synthesizing the second base component and the detail component to output a synthesized signal. The color enhancement process includes converting the first base component including an R component, a G component, and a B component into an L component, an a component, and a b component in an Lab color space, performing an enhancement process on the a component for extending a color distribution range, performing an enhancement process on the b component for extending a color distribution range, and converting the a component subjected to the enhancement process, the b component subjected to the enhancement process, and the L component into the second base component including an R component, a G component, and a B component.

In some embodiments, an image processing method includes: dividing an imaging signal that is obtained by capturing an image of inside of a subject into a base component and a detail component, the base component corresponding to an illumination component of an object, the detail component corresponding to a reflectance component of the object; performing a predetermined enhancement process on at least one of the base component and the detail component; after the predetermined enhancement process, synthesizing the base component and the detail component to output a first synthesized signal; outputting a second synthesized signal that is obtained by performing a color enhancement process on the output first synthesized signal, the color enhancement process being a process of increasing color gradation of a mucosa color on a predetermined color space. The color enhancement process includes converting the first synthesized signal including an R component, a G component, and a B component into an L component, an a component, and a b component in an Lab color space, performing an enhancement process on the a component for extending a color distribution range, performing an enhancement process on the b component for extending a color distribution range, and converting the a component subjected to the enhancement process, the b component subjected to the enhancement process, and the L component into the second synthesized signal including an R component, a G component, and a B component.

The above and other features, advantages and technical and industrial significance of this disclosure will be better understood by reading the following detailed description of presently preferred embodiments of the disclosure, when considered in connection with the accompanying drawings.

DETAILED DESCRIPTION

As modes (hereinafter, referred to as "embodiments") for carrying out the present disclosure, an endoscope system including an endoscope that captures an image of inside of a body cavity of a subject, such as a patient, and displays the image will be described below as an example. Further, the present disclosure is not limited by the embodiments below. Furthermore, in description of the drawings, the same components are denoted by the same reference symbols.

First Embodiment

Configuration of Endoscope System

Figure 1:
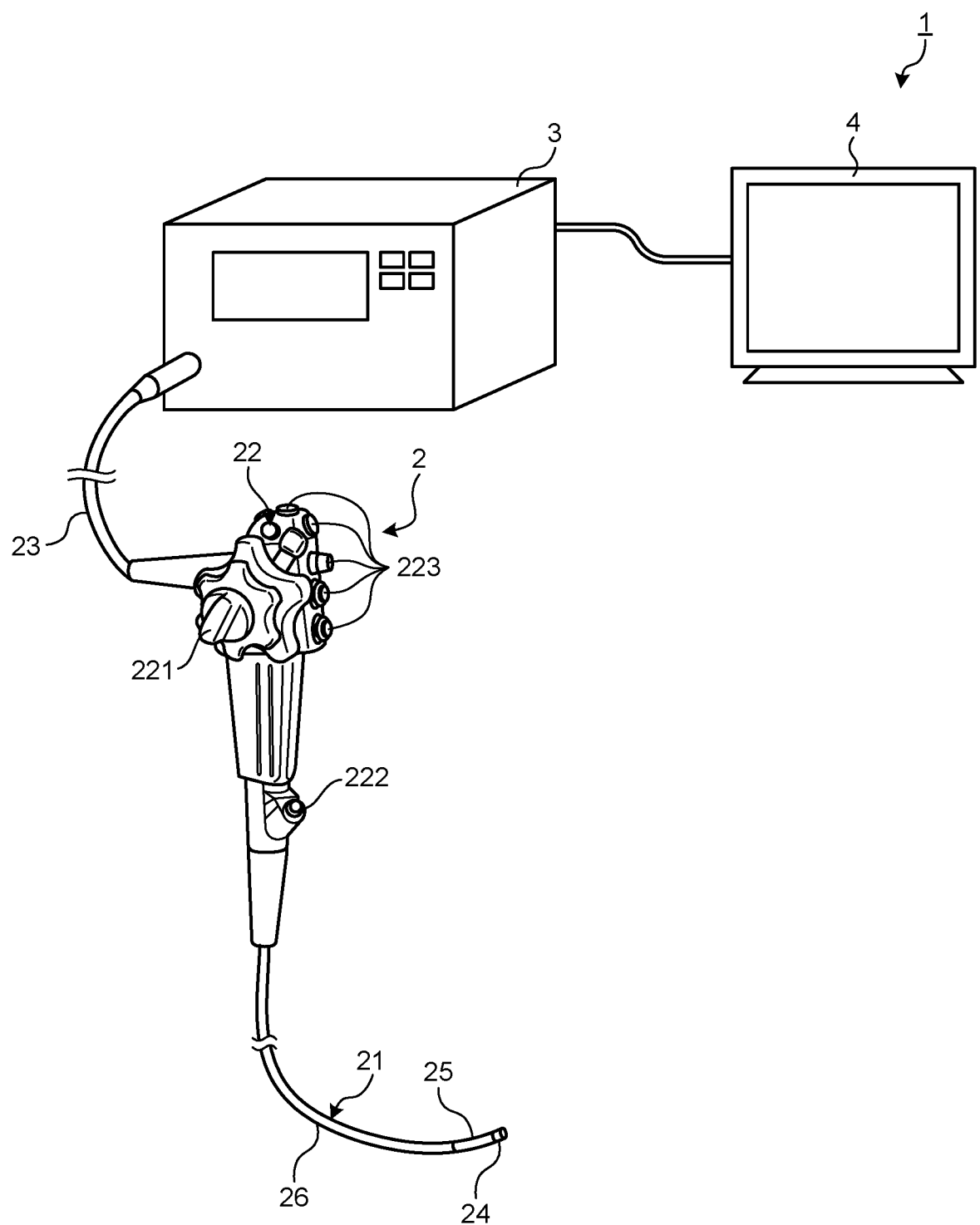
FIG. 1 is a diagram illustrating a schematic configuration of an endoscope system according to a first embodiment of the present disclosure.
Figure 2:
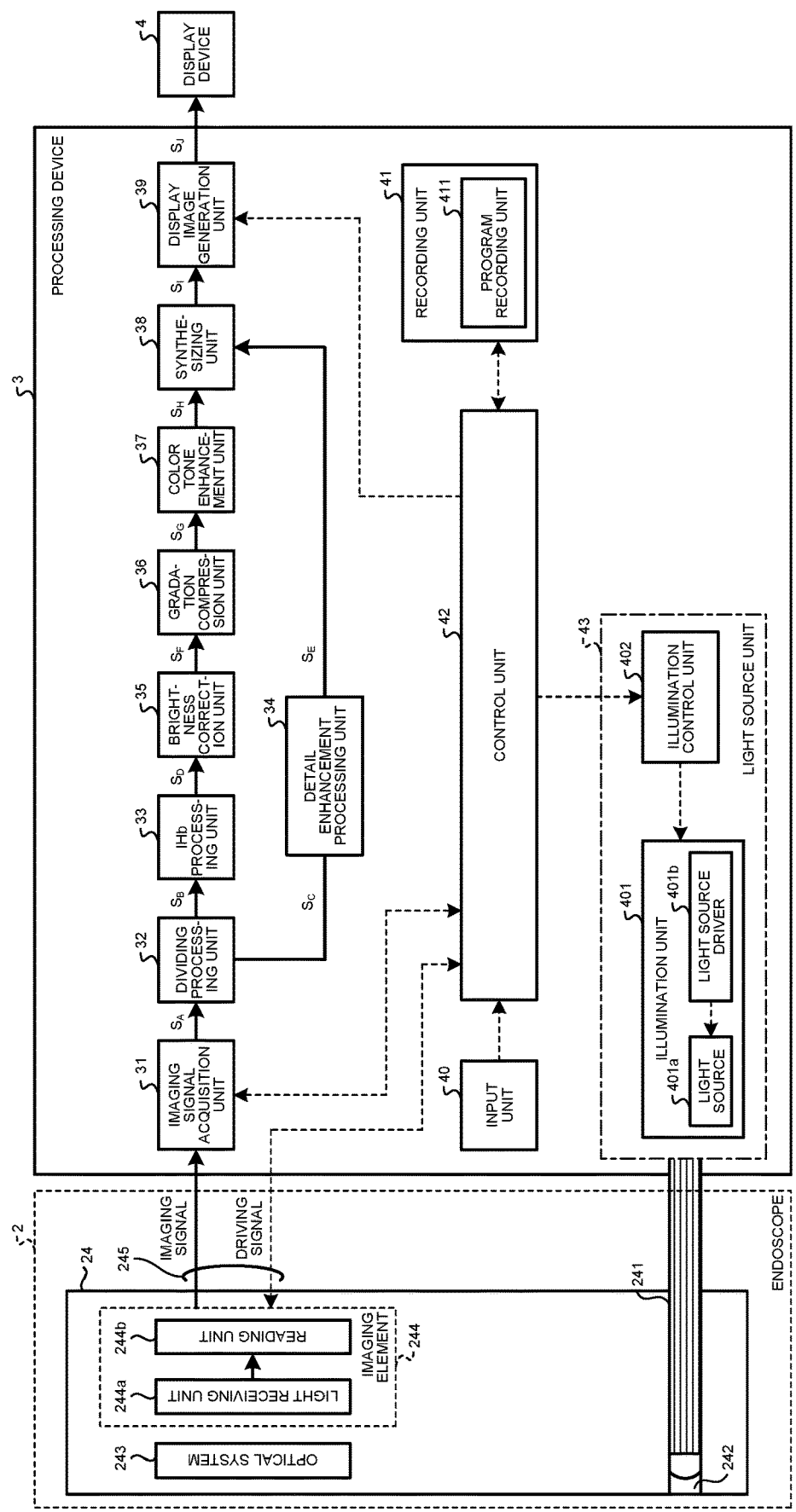
FIG. 2 is a block diagram illustrating a functional configuration of an endoscope system according to the first embodiment of the present disclosure.

FIG. 1 is a diagram illustrating a schematic configuration of an endoscope system according to a first embodiment of the present disclosure. FIG. 2 is a block diagram illustrating a functional configuration of the endoscope system according to the first embodiment of the present disclosure.

An endoscope system 1 illustrated in FIG. 1 and FIG. 2 includes an endoscope 2, a distal end of which is inserted into a subject and which captures an in-vivo image of the subject by emitting illumination light from the distal end, a processing device 3 that includes a light source unit 43 for generating illumination light to be emitted from the distal end of the endoscope 2, that performs predetermined image processing on an imaging signal captured by the endoscope 2, and that comprehensively controls entire operation of the endoscope system 1, and a display device 4 that displays an image corresponding to the imaging signal that is subjected to signal processing by the processing device 3.

Configuration of Endoscope

First, a detailed configuration of the endoscope 2 will be described.

The endoscope 2 includes a flexible insertion portion 21 that has a thin and elongated shape, an operation unit 22 that is connected to a proximal end side of the insertion portion 21 and that receives input of various operation signals, and a universal cord 23 that extends in a direction different from a direction in which the insertion portion 21 extends from the operation unit 22 and that has various built-in cables connected to the processing device 3 (including the light source unit 43).

The insertion portion 21 includes a distal end portion 24 that includes a built-in imaging element 244, in which pixels that receive light and generate signals by performing photoelectric conversion are arranged two-dimensionally, a bending portion 25 that includes a plurality of bending pieces and that is freely bendable, and a flexible tube portion 26 that is connected to a proximal end side of the bending portion 25, that is flexible, and that has an elongated shape. The insertion portion 21 is inserted into a subject and captures, by the imaging element 244, an image of an object, such as a living tissue, that is located at a position where external light does not reach.

The distal end portion 24 includes a light guide 241 that is configured with fiberglass or the like and serves as a light guide for light emitted by the light source unit 43, an illumination lens 242 that is arranged at a distal end of the light guide 241, an optical system 243 that condenses light, and the imaging element 244 that is arranged at an image forming position of the optical system 243, receives light condensed by the optical system 243, performs photoelectric conversion on the light to obtain an electrical signal, and performs predetermined signal processing on the electrical signal.

The optical system 243 is configured with one or more lenses, and has an optical zoom function to change an angle of view and a focus function to change a focal point.

The imaging element 244 performs photoelectric conversion on light coming from the optical system 243 to generate an electrical signal (imaging signal), and outputs the electrical signal to the processing device 3. Specifically, the imaging element 244 includes a light receiving unit 244a that includes a plurality of pixels, each of which includes a photodiode for accumulating charges corresponding to light intensity and a capacitor for converting charges transferred from the photodiode into voltage levels, which are arranged in a matrix manner, and each of which performs photoelectric conversion on light coming from the optical system 243 to generate an electrical signal, and a reading unit 244b that sequentially reads electrical signals that are generated by pixels that are arbitrarily set as read targets among the plurality of pixels included in the light receiving unit 244a, and outputs the read electrical signals as imaging signals. The light receiving unit 244a includes a color filter, and each of the pixels receives light of any of wavelength bands of a plurality of color components, such as red (R), green (G), and blue (B). The imaging element 244 controls various kinds of operation of the distal end portion 24 in accordance with a driving signal received from the processing device 3. The imaging element 244 is realized by using, for example, a charge coupled device (CCD) image sensor or a complementary metal oxide semiconductor (CMOS) image sensor.

The operation unit 22 includes a bending knob 221 that causes the bending portion 25 to bend in a vertical direction and in a horizontal direction, a treatment tool insertion portion 222 for inserting a treatment tool, such as a biopsy forceps, an electric scalpel, and an inspection probe, into a subject, and a plurality of switches 223 that are operation input units for inputting operation instruction signals for peripheral devices, such as an air supply unit, a water supply unit, and a screen display control, in addition to the processing device 3. The treatment tool inserted from the treatment tool insertion portion 222 is exposed from an opening portion (not illustrated) through a treatment channel (not illustrated) of the distal end portion 24.

The universal cord 23 incorporates at least the light guide 241 and an assembly cable 245 in which one or more signal lines are assembled. The assembly cable 245 includes a signal line for transferring an imaging signal, a signal line for transferring a driving signal for driving the imaging element 244, and a signal line for transmitting and receiving information including unique information on the endoscope 2 (the imaging element 244). Meanwhile, in the first embodiment, it is explained that electrical signals are transferred using the signal lines, but it may be possible to provide an electrical-to-optical (E/O) conversion circuit in the distal end portion 24 and transfer optical signals, or it may be possible to provide a communication module or the like in the distal end portion 24 and transfer imaging signals between the endoscope 2 and the processing device 3 via radio communication. It may of course be possible to provide an analog-to-digital (A/D) conversion circuit in the distal end portion 24, perform A/D conversion on an imaging signal, and output a digital imaging signal to the processing device 3.

Configuration of Processing Device

A configuration of the processing device 3 will be described below.

The processing device 3 includes an imaging signal acquisition unit 31, a dividing processing unit 32, an IHb processing unit 33, a detail enhancement processing unit 34, a brightness correction unit 35, a gradation compression unit 36, a color tone enhancement unit 37, a synthesizing unit 38, a display image generation unit 39, an input unit 40, a recording unit 41, a control unit 42, and the light source unit 43. Meanwhile, the image processing apparatus according to the first embodiment is configured with at least the dividing processing unit 32, the IHb processing unit 33, the detail enhancement processing unit 34, the brightness correction unit 35, the gradation compression unit 36, the color tone enhancement unit 37, and the synthesizing unit 38. Further, the image processing apparatus according to the first embodiment is configured to implement functions of at least the dividing processing unit 32, the IHb processing unit 33, the detail enhancement processing unit 34, the brightness correction unit 35, the gradation compression unit 36, the color tone enhancement unit 37, and the synthesizing unit 38 by using a field programmable gate array (FPGA), an application specific integrated circuit (ASIC), a graphics processing unit (GPU), or the like.

The imaging signal acquisition unit 31 receives an imaging signal output from the imaging element 244 of the endoscope 2, performs predetermined image processing on the received imaging signal, and outputs the imaging signal to the dividing processing unit 32. Here, as the predetermined image processing, a noise removal process of removing noise from the imaging signal, an A/D conversion process of converting an analog imaging signal to a digital imaging signal, a synchronization process, and the like are performed.

The dividing processing unit 32 performs a dividing process on an imaging signal $S_A$ input from the imaging signal acquisition unit 31, and divides the imaging signal $S_A$ into a visually weakly correlated component and a visually strongly correlated component. Here, the dividing process may be performed by using, for example, a technology (Retinex theory) described in Lightness and retinex theory, E. H. Land, J. J. McCann, Journal of the Optical Society of America, 61(1), 1-11 (1971). In the dividing process based on the Retinex theory, the visually weakly correlated component corresponds to an illumination component of an object and is generally called a base component. In contrast, in the dividing process based on the Retinex theory, the visually strongly correlated component corresponds to a reflectance component of an object and is generally called a detail component. The detail component is a component that is obtained by dividing a signal constituting an image by the base component. The detail component includes a contrast component, such as a contour (edge) component or a texture component, of an object. The dividing processing unit 32 outputs a signal including the base component (hereinafter, referred to as a "base component signal $S_B$") to the IHb processing unit 33, and outputs a signal including the detail component (hereinafter, referred to as a "detail component signal $S_C$") to the detail enhancement processing unit 34. Meanwhile, the dividing processing unit 32 may perform a component dividing process by using, for example, an Edge-aware filtering technology described in Temporally Coherent Local Tone Mapping of HDR Video, T. O. Aydin, et al., ACM Transactions on Graphics, Vol 33, November 2014, or by dividing a spatial frequency into a plurality of frequency bands. Further, if the imaging signal $S_A$ of each of color components of R, G, and B is input, the dividing processing unit 32 performs the above-described dividing process on each of the imaging signals of the plurality of color components. Similarly, in subsequent signal processing, the process is performed for each of the color components.

The IHb processing unit 33 performs a hemoglobin index color enhancement process (hereinafter, referred to as an "IHb color enhancement process") on the base component signal $S_B$ input from the dividing processing unit 32, and outputs a base component signal $S_D$ subjected to the IHb color enhancement process to the brightness correction unit 35. Here, the IHb color enhancement process is a process of calculating an approximate mucosal blood flow by performing inter-image operation on each of images corresponding to the base component signals $S_B$ of the respective color components of R, G, and B.

The detail enhancement processing unit 34 performs a detail enhancement process of enhancing the detail component on the detail component signal $S_C$ input from the dividing processing unit 32, and outputs a detail component signal $S_E$ subjected to the detail enhancement process to the synthesizing unit 38. Here, the detail enhancement process is a process of enhancing a contrast component, such as a contour component and a texture component of an object.

The brightness correction unit 35 performs a brightness adjustment process on the base component signal $S_D$ input from the IHb processing unit 33, and outputs a base component signal $S_F$ subjected to the brightness adjustment process to the gradation compression unit 36. Here, the brightness adjustment process is a process of performing, for example, a gain-up process of increasing a low luminance value on the basis of a luminance value at each of pixel positions. Meanwhile, the brightness correction unit 35 may perform the gain-up process or the like by performing an arithmetic process on the base component signal $S_D$.

The gradation compression unit 36 performs a gradation compression process on the base component signal $S_F$ input from the brightness correction unit 35, and outputs a base component signal $S_G$ subjected to the gradation compression process to the color tone enhancement unit 37. Here, the gradation compression process is a gamma process or the like.

The color tone enhancement unit 37 performs a color tone enhancement process of enhancing color tone on the base component signal $S_G$ input from the gradation compression unit 36, and outputs a base component signal $S_H$ subjected to the color tone enhancement process to the synthesizing unit 38. Specifically, the color tone enhancement unit 37 performs a conversion process such that a mucosa color, which is distributed in a narrow red region, is distributed in a wider region. For example, the color tone enhancement unit 37 performs a process of increasing gradation such that an original mucosa color distributed in a narrow red region is distributed even in a purple region. Meanwhile, the color tone enhancement process will be described in detail later.

The synthesizing unit 38 synthesizes the detail component signal $S_E$ input from the detail enhancement processing unit 34 and the base component signal $S_H$ input from the color tone enhancement unit 37, and outputs a synthesized signal $S_I$ to the display image generation unit 39. By synthesizing the detail component signal $S_E$ and the base component signal $S_H$, the synthesizing unit 38 is able to generate the synthesized signal $S_I$ such that the mucosa color distribution range is extended only for a visually weakly correlated base component.

The display image generation unit 39 generates an image signal $S_J$ for display by performing, on the synthesized signal $S_I$ input from the synthesizing unit 38, signal processing for obtaining a signal in a certain mode that can be displayed by the display device 4, and outputs the image signal $S_J$ to the display device 4. If the synthesized signal $S_I$ input from the synthesizing unit 38 is divided into each of color components of R, G, and B, the display image generation unit 39 performs an interpolation process on each of the color components to generate an image signal in which RGB color components are added to each of the pixel positions, and outputs the image signal to the display device 4.

The input unit 40 is realized by using a keyboard, a mouse, a switch, or a touch panel, and receives input of various signals, such as an operation instruction signal for giving an instruction on operation of the endoscope system 1. Meanwhile, the input unit 40 may include a switch arranged on the operation unit 22 or a portable terminal, such as an external tablet computer.

The recording unit 41 stores therein various programs for operating the endoscope system 1 and data including various parameters or the like needed for operation of the endoscope system 1. The recording unit 41 includes a program recording unit 411 that records therein various programs to be executed by the endoscope system 1. The recording unit 41 is configured with a flash memory, a synchronous dynamic random access memory (SDRAM), a memory card, or the like.

The control unit 42 is configured with a central processing unit (CPU) or the like, controls drive of each of structural units including the imaging element 244 and the light source unit 43, and controls input and output of data to and from each of the structural units. The control unit 42 refers to control information data (for example, a read timing or the like) that is used for controlling imaging and that is stored in the recording unit 41, and transmits the control information data as a driving signal to the imaging element 244 via a predetermined signal line included in the assembly cable 245.

Configuration of Light Source Unit

A configuration of the light source unit 43 will be described below.

The light source unit 43 includes an illumination unit 401 and an illumination control unit 402. The illumination unit 401 emits illumination light at different exposures in a sequentially switching manner to an object (subject), under the control of the illumination control unit 402. The illumination unit 401 includes a light source 401a and a light source driver 401b.

The light source 401a is configured with an LED light source that emits white light, one or more lenses, and the like, and emits light (illumination light) by drive of the LED light source. The illumination light generated by the light source 401a is emitted from a distal end of the distal end portion 24 to the object via the light guide 241. Meanwhile, the light source 401a may be configured with a red LED light source, a green LED light source, and a blue LED light source, and emit illumination light. Further, the light source 401a may use a laser light source or a lamp, such as a xenon lamp or a halogen lamp.

The light source driver 401b supplies electric current to the light source 401a and causes the light source 401a to emit illumination light, under the control of the illumination control unit 402.

The illumination control unit 402 controls an amount of power to be supplied to the light source 401a and a driving timing of the light source 401a, on the basis of a control signal (light adjustment signal) received from the control unit 42.

Configuration of Display Device

A configuration of the display device 4 will be described below.

The display device 4 displays, via a video cable, an image corresponding to the image signal $S_J$ generated by the processing device 3 (the display image generation unit 39).

The display device 4 is configured with a monitor, such as a liquid crystal monitor or an organic electro luminescence (EL) monitor.

Outline of Color Tone Enhancement Process

Figure 3A:
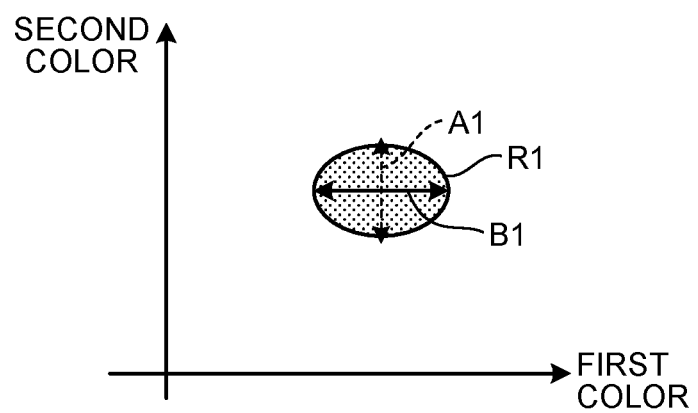
FIG. 3A is a schematic diagram illustrating a mucosa color distribution range before a color tone enhancement process is performed.
Figure 3B:
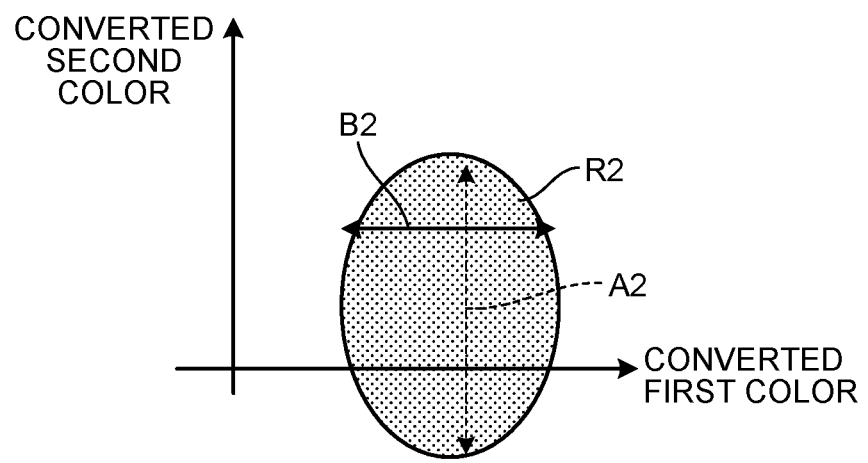
FIG. 3B is a schematic diagram illustrating a mucosa color distribution range after the color tone enhancement process is performed.
Figure 4A:
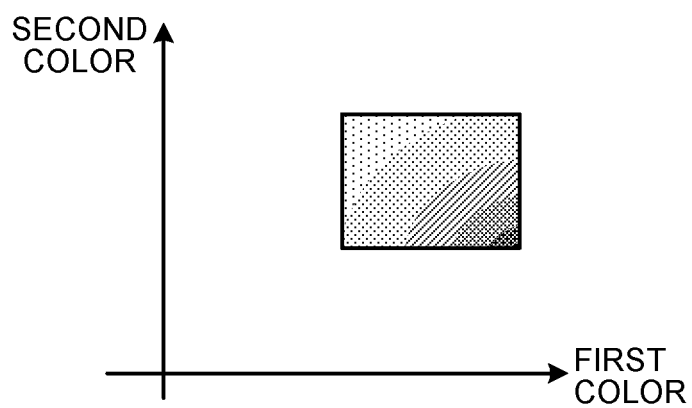
FIG. 4A is a schematic diagram illustrating a color distribution before the color tone enhancement process is performed.
Figure 4B:
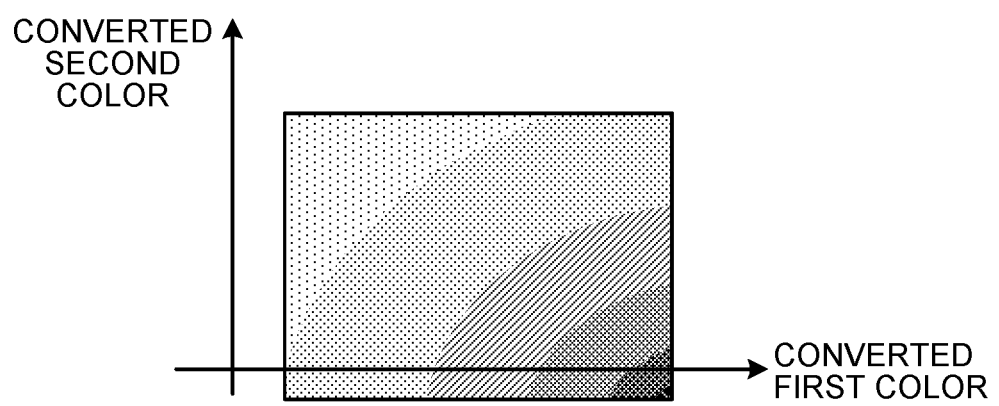
FIG. 4B is a schematic diagram illustrating an effect of a color distribution after the color tone enhancement process is performed.

An outline of the color tone enhancement process performed by the color tone enhancement unit 37 as described above will be described below. FIG. 3A is a schematic diagram illustrating a mucosa color distribution range before the color tone enhancement process is performed, FIG. 3B is a schematic diagram illustrating a mucosa color distribution range after the color tone enhancement process is performed, FIG. 4A is a schematic diagram illustrating a color distribution before the color tone enhancement process is performed, and FIG. 4B is a schematic diagram illustrating an effect of a color distribution after the color tone enhancement process is performed. In FIG. 3A and FIG. 4A, horizontal axes represent a first color, and vertical axes represent a second color. Further, in FIG. 3B and FIG. 4B, horizontal axes represent a converted first color that is obtained after gradation is enhanced using a conversion function for the first color, and vertical axes represent a converted second color that is obtained after gradation is enhanced using a conversion function for the second color.

As illustrated in FIG. 3A and FIG. 3B, the color tone enhancement unit 37 obtains an enhanced mucosa color distribution range R2 by performing an enhancement process on a mucosa color distribution range R1 (FIG. 3A→FIG. 3B). Specifically, the color tone enhancement unit 37 enhances gradation from a range B1 of the first color (red color component) in the mucosa color distribution range R1 to a range B2 of the first color in the mucosa color distribution range R2 by applying the conversion function for the first color. Further, the color tone enhancement unit 37 enhances gradation from a range A1 of the second color (blue color component) in the mucosa color distribution range R1 to a range A2 of the second color in the mucosa color distribution range R2 by applying the conversion function for the second color. With this operation, as illustrated in FIG. 4A and FIG. 4B, an enhancement process is performed such that a mucosa color that is distributed in a narrow red region is distributed in a wider region, so that color gradation property is improved and it is possible to easily recognize a change of color tone among a normal mucosa, inflammation, and an early tumor lesion.

Process Performed by Processing Device

Figure 5:
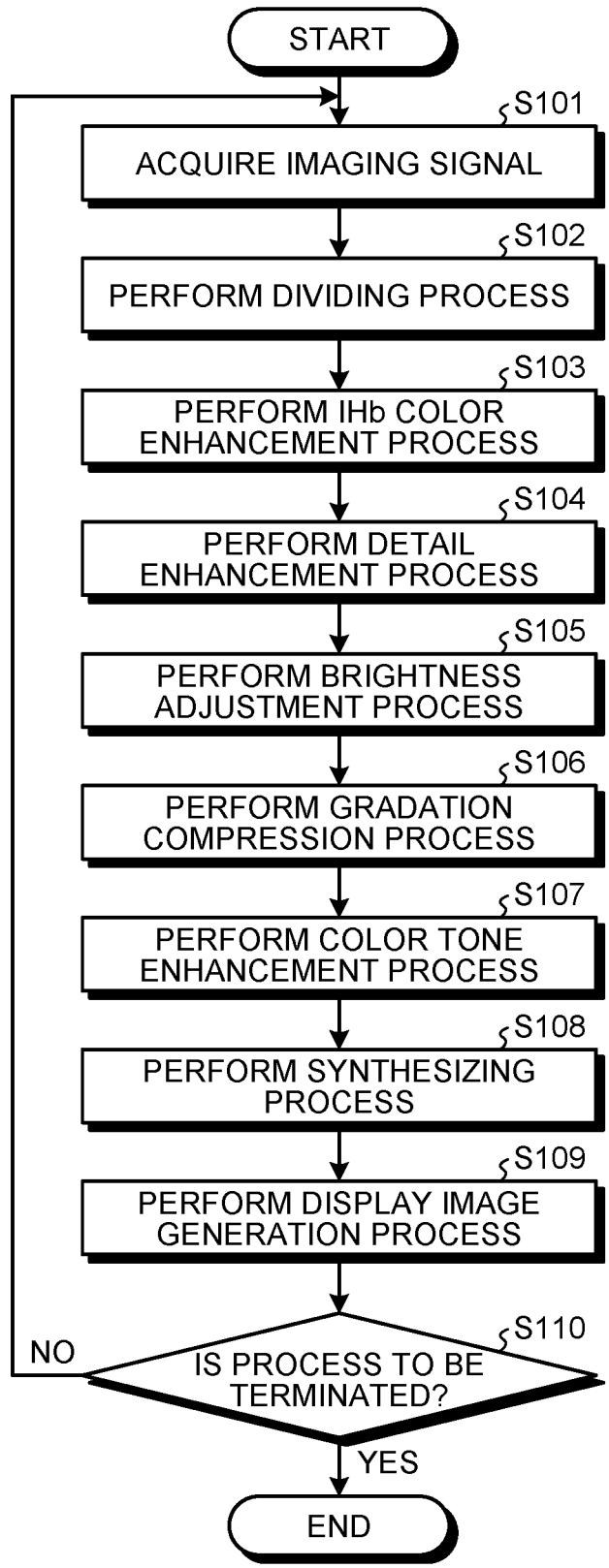
FIG. 5 is a flowchart illustrating an outline of a process performed by a processing device according to the first embodiment of the present disclosure.

A process performed by the processing device will be described below. FIG. 5 is a flowchart illustrating an outline of a process performed by the processing device 3.

First, as illustrated in FIG. 5, the imaging signal acquisition unit 31 receives and acquires an imaging signal output from the imaging element 244 of the endoscope 2 (Step S101). In this case, the imaging signal acquisition unit 31 performs predetermined image processing on the imaging signal that is received and acquired from the imaging element 244, and outputs the imaging signal to the dividing processing unit 32.

Subsequently, the dividing processing unit 32 performs a dividing process of dividing the imaging signal $S_A$ input from the imaging signal acquisition unit 31 into the base component signal $S_B$ and the detail component signal $S_C$ (Step S102).

Thereafter, the IHb processing unit 33 performs an IHb color enhancement process on the base component signal $S_B$ input from the dividing processing unit 32 (Step S103).

Subsequently, the detail enhancement processing unit 34 performs a detail enhancement process of enhancing a detail component of the detail component signal $S_C$ input from the dividing processing unit 32 (Step S104).

Thereafter, the brightness correction unit 35 performs a brightness adjustment process on the base component signal $S_D$ input from the IHb processing unit 33 (Step S105).

Subsequently, the gradation compression unit 36 performs a gradation compression process on the base component signal $S_F$ input from the brightness correction unit 35 (Step S106).

Thereafter, the color tone enhancement unit 37 performs a color tone enhancement process of enhancing color tone on the base component signal $S_G$ input from the gradation compression unit 36 (Step S107).

Subsequently, the synthesizing unit 38 performs a synthesizing process of synthesizing the detail component signal $S_E$ input from the detail enhancement processing unit 34 and the base component signal $S_H$ input from the color tone enhancement unit 37 (Step S108).

Thereafter, the display image generation unit 39 performs a display image generation process of generating a signal in a certain mode that can be displayed by the display device 4, on the synthesized signal $S_I$ input from the synthesizing unit 38 (Step S109).

Subsequently, if an instruction signal for giving an instruction on termination is input from the input unit 40 (Step S110: Yes), the processing device 3 terminates the process. In contrast, if the instruction signal for giving an instruction on termination is not input from the input unit 40 (Step S110: No), the processing device 3 returns to Step S101 described above.

According to the first embodiment of the present disclosure as described above, the synthesizing unit 38 synthesize the base component subjected to the color enhancement process by the color tone enhancement unit 37 and the detail component, and outputs a synthesized signal; therefore, it is possible to easily recognize a change of color tone between a normal mucosa and an abnormal mucosa.

Furthermore, according to the first embodiment of the present disclosure, the color tone enhancement unit 37 performs the color tone enhancement process on at least a blue component on the basis of a value that is standardized by a red color component; therefore, it is possible to improve color gradation property, and it becomes possible to easily recognize a change of color tone among a normal mucosa, inflammation, and an early tumor lesion.

Second Embodiment

A second embodiment of the present disclosure will be described below. The second embodiment is different from the first embodiment of the present disclosure in terms of the color tone enhancement unit 37. Specifically, in the first embodiment as described above, the color tone enhancement unit 37 enhances the mucosa color distribution range in the base component signal of each of color components of R, G, and B; however, in the second embodiment, the color tone enhancement unit 37 enhances a mucosa color distribution range in a Lab color space. Therefore, in the following, a configuration of a color tone enhancement unit according to the second embodiment will be described. Meanwhile, the same components as those of the endoscope system 1 according to the first embodiment as described above are denoted by the same reference symbols, and explanation thereof will be omitted.

Configuration of Color Tone Enhancement Unit

Figure 6:
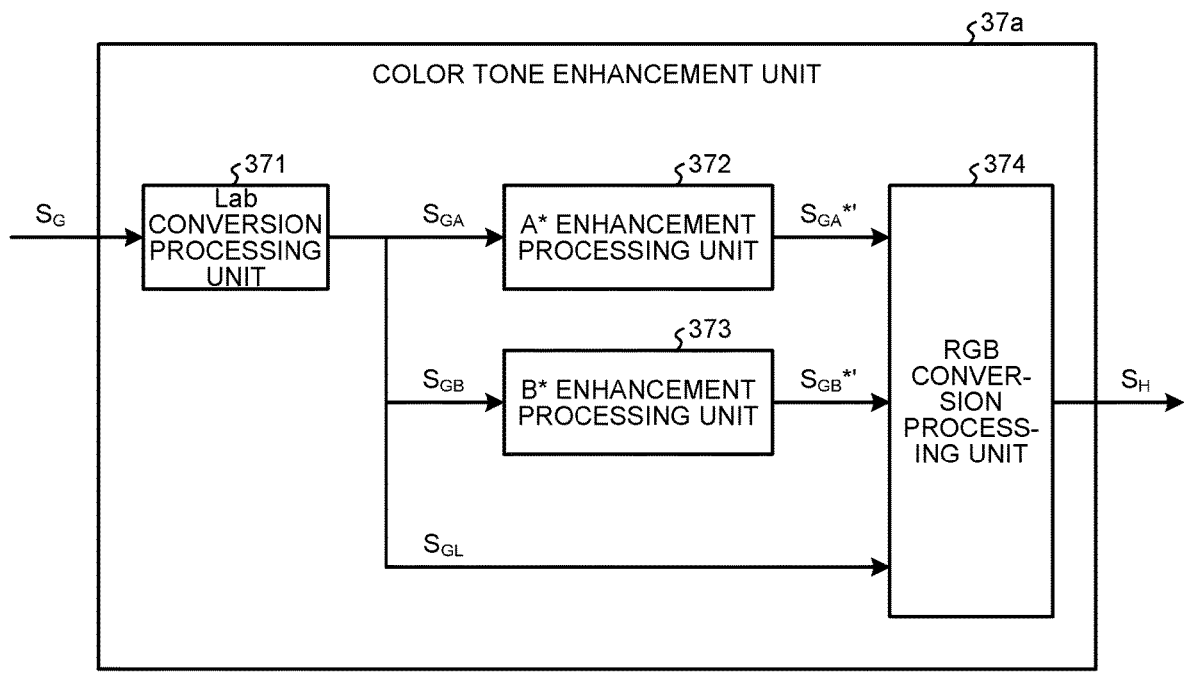
FIG. 6 is a block diagram illustrating a functional configuration of a color tone enhancement unit according to a second embodiment of the present disclosure.

FIG. 6 is a block diagram illustrating a functional configuration of the color tone enhancement unit according to the second embodiment. A color tone enhancement unit 37a illustrated in FIG. 6 performs a color tone enhancement process of increasing color gradation of a base component by using a predetermined conversion function in the Lab color space, and outputs a base component signal $S_H$ subjected to the color tone enhancement process to the synthesizing unit 38. The color tone enhancement unit 37a includes a Lab conversion processing unit 371, an A* enhancement processing unit 372, a B* enhancement processing unit 373, and an RGB conversion processing unit 374.

The Lab conversion processing unit 371 converts the base component signal $S_G$ of each of color components of R, G, and B input from the gradation compression unit 36 into the Lab color space. A base component signal $S_{GA}$ converted for the Lab color space is output to the A* enhancement processing unit 372. Further, a base component signal $S_{GB}$ converted for the Lab color space is input to the B* enhancement processing unit 373, a base component signal $S_{GL}$ converted for the Lab color space is input to the RGB conversion processing unit 374.

The A* enhancement processing unit 372 performs an enhancement process using a predetermined function on the base component signal $S_{GA}$ input from the Lab conversion processing unit 371, and outputs a base component signal $S_{GA}{*}'$ subjected to the enhancement process to the RGB conversion processing unit 374. Specifically, the A* enhancement processing unit 372 extends the mucosa color distribution range by performing the enhancement process on the mucosa color distribution range with respect to the base component signal $S_{GA}$ input from the Lab conversion processing unit 371. More specifically, assuming that the base component signal $S_{GA}$ is represented by a* and the base component signal $S_{GA}{*}'$ is represented by with respect to the base component signal $S_{GA}$ input from the Lab conversion processing unit 371, the A* enhancement processing unit 372 performs the enhancement process using Equation (1) below.

$$a{*}' = f(a{*}) \quad (1)$$

The B* enhancement processing unit 373 performs an enhancement process using a predetermined function on the base component signal $S_{GB}$ input from the Lab conversion processing unit 371, and outputs a base component signal $S_{GB}{*}'$ subjected to the enhancement process to the RGB conversion processing unit 374. Specifically, the B* enhancement processing unit 373 extends the mucosa color distribution range by performing the enhancement process on the mucosa color distribution range with respect to the base component signal $S_{GB}$ input from the Lab conversion processing unit 371 by using, as an input argument, a value that is standardized by a* by the A* enhancement processing unit 372. More specifically, assuming that the base component signal $S_{GB}$ is represented by b* and the base component signal $S_{GB}{*}'$ is represented by b*' with respect to the base component signal $S_{GB}$ input from the Lab conversion processing unit 371, the B* enhancement processing unit 373 first calculates the input argument by Equation (2) below.

$$\text{Input argument} = b{*}/a{*} \quad (2)$$

Then, the B* enhancement processing unit 373 performs the enhancement process on the base component signal $S_{GB}$ input from the Lab conversion processing unit 371 by Equation (3) below.

$$b{*}'/a{*} = g(b{*}/a{*}) \quad (3)$$

That is, Equation (4) below is obtained.

$$b{*}' = g(b{*}/a{*})a{*} \quad (4)$$

The RGB conversion processing unit 374 performs an RGB conversion process on the base component signal $S_{GA}{*}'$ input from the A* enhancement processing unit 372, the base component signal $S_{GB}{*}'$ input from the B* enhancement processing unit 373, and the base component signal $S_{GL}$ input from the Lab conversion processing unit 371 to perform conversion to the base component signal $S_H$ of each of color components of R, G, and B, and outputs the base component signal $S_H$ to the synthesizing unit 38.

Outline of Color Tone Enhancement Process

Figure 7A:
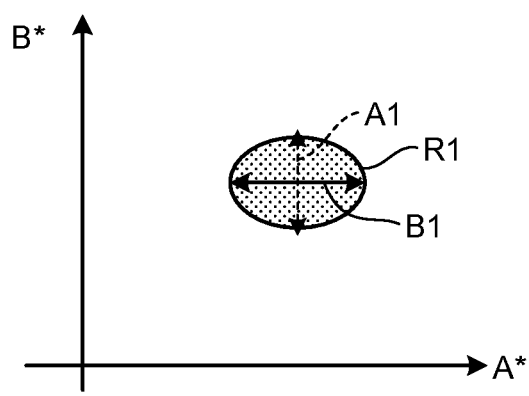
FIG. 7A is a schematic diagram illustrating a mucosa color distribution range before a color tone enhancement process is performed.
Figure 7B:
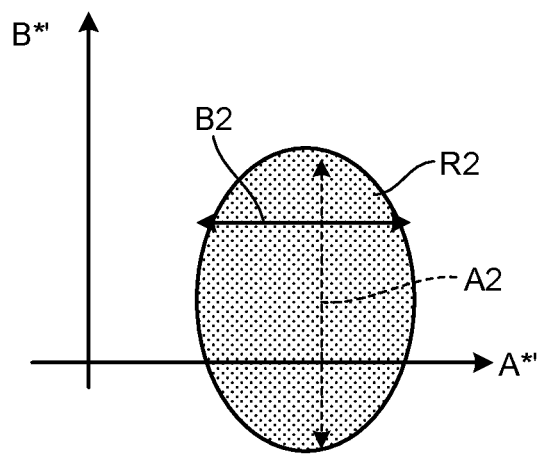
FIG. 7B is a schematic diagram illustrating a mucosa color distribution range after the color tone enhancement process is performed.
Figure 8A:
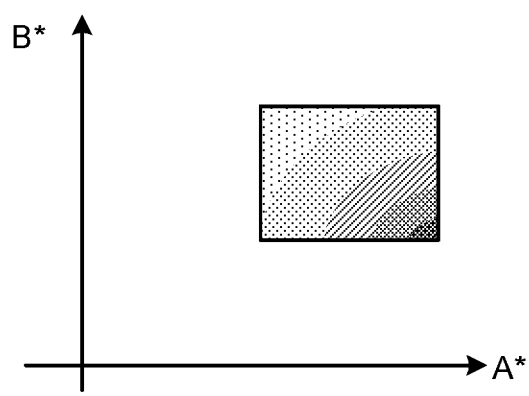
FIG. 8A is a schematic diagram illustrating a color distribution before the color tone enhancement process is performed.
Figure 8B:
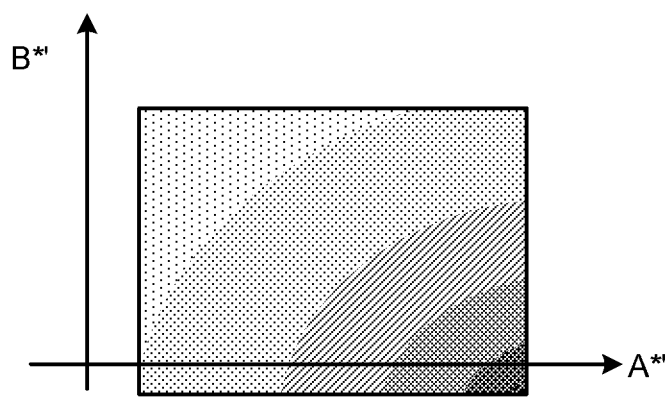
FIG. 8B is a schematic diagram illustrating a color distribution after the color tone enhancement process is performed.

An outline of a color tone enhancement process performed by the color tone enhancement unit 37a as described above will be described below. FIG. 7A is a schematic diagram illustrating a mucosa color distribution range before the color tone enhancement process is performed, FIG. 7B is a schematic diagram illustrating a mucosa color distribution range after the color tone enhancement process is performed, FIG. 8A is a schematic diagram illustrating a color distribution before the color tone enhancement process is performed, and FIG. 8B is a schematic diagram illustrating a color distribution after the color tone enhancement process is performed. In FIG. 7A and FIG. 8A, horizontal axes represent A*, and vertical axes represent B*. Further, in FIG. 7B and FIG. 8B, horizontal axes represent converted A*' that is obtained after gradation is enhanced using a conversion function for A*, and vertical axes represent converted B*' that is obtained after gradation is enhanced using a conversion function for B*.

As illustrated in FIG. 7A and FIG. 7B, the color tone enhancement unit 37a obtains an enhanced mucosa color distribution range R2 by performing an enhancement process on the mucosa color distribution range R1 (FIG. 7A→FIG. 7B). Specifically, the color tone enhancement unit 37a enhances gradation from the range B1 of A* (red color component) in the mucosa color distribution range R1 to the range B2 of A* in the mucosa color distribution range R2 by applying a conversion function of A*. Further, the color tone enhancement unit 37a enhances gradation from the range A1 of B* (blue color component) in the mucosa color distribution range R1 to the range A2 of B* in the mucosa color distribution range R2 by applying a conversion function using a value of BB*/A* as input. With this operation, as illustrated in FIG. 8A and FIG. 8B, an enhancement process is performed such that a mucosa color distributed in a narrow red region is distributed in a wider region, so that color gradation property is improved and it is possible to easily recognize a change of color tone among a normal mucosa, inflammation, and an early tumor lesion.

According to the second embodiment of the present disclosure as described above, the color tone enhancement unit 37a increases color gradation of a mucosa color by applying a predetermined conversion function to a base component in the Lab color space, so that it is possible to easily recognize a change of color tone between a normal mucosa and an abnormal mucosa.

Meanwhile, in the second embodiment of the present disclosure, the color tone enhancement unit 37a converts the base component into the Lab color space, but embodiments are not limited to this example, and it may be possible to perform a process of increasing color gradation in other color spaces, such as RGB or YCbCr.

Furthermore, in the second embodiment of the present disclosure, the color tone enhancement unit 37a may perform a conversion process on a brightness component of the base component signal $S_{GL}$ on the basis of a value that is standardized by a red color component.

First Modification of First and Second Embodiments

Figure 9:
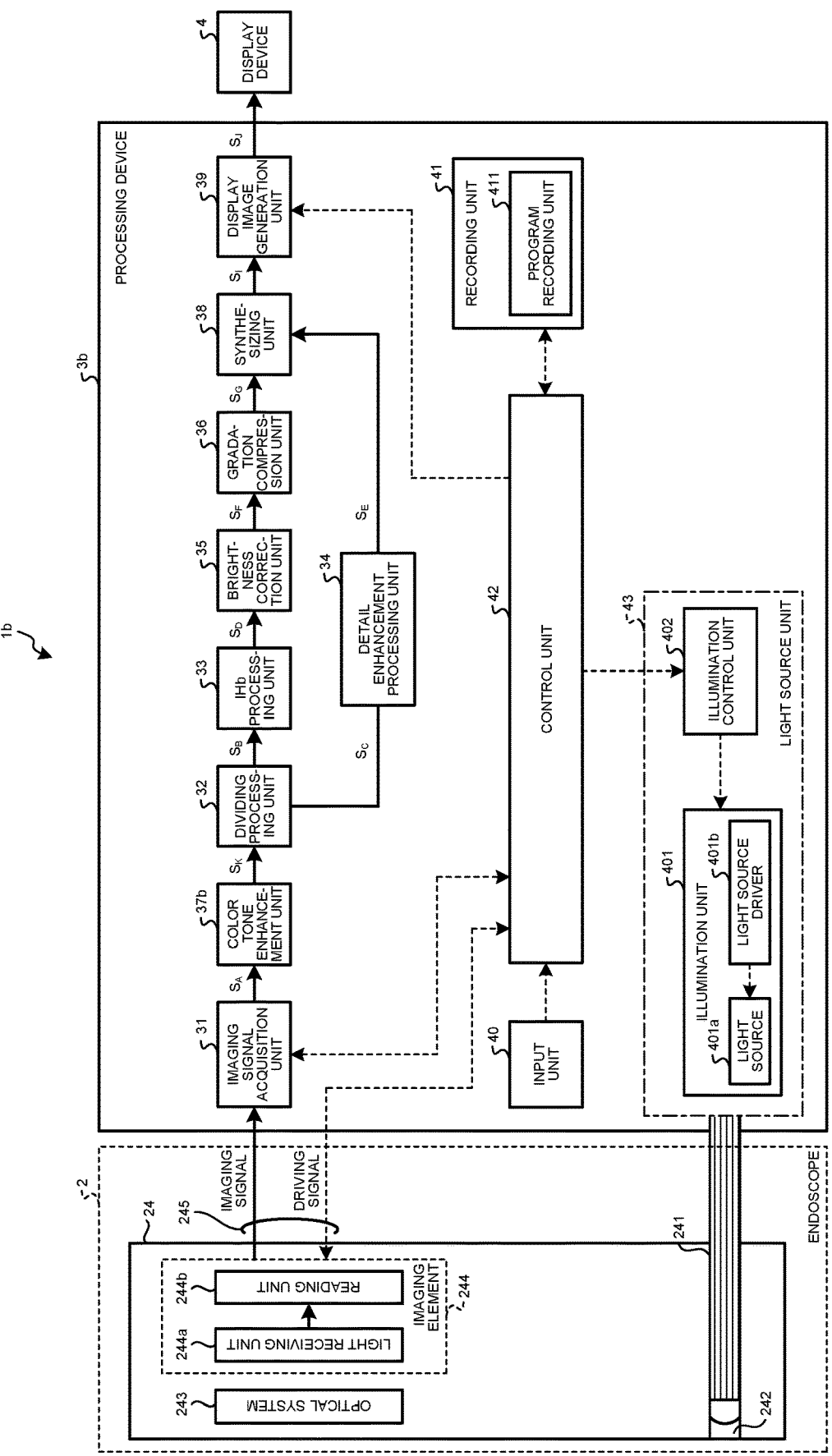
FIG. 9 is a block diagram illustrating a functional configuration of an endoscope system according to a first modification of the first and the second embodiments of the present disclosure.

A first modification of the first and the second embodiments of the present disclosure will be described. FIG. 9 is a block diagram illustrating a functional configuration of an endoscope system according to the first modification of the first and the second embodiments of the present disclosure.

An endoscope system 1b illustrated in FIG. 9 includes a processing device 3b instead of the processing device 3 of the endoscope system 1 according to the first embodiment as described above. The processing device 3b includes a color tone enhancement unit 37b instead of the color tone enhancement unit 37 of the processing device 3 according to the first embodiment as described above.

The color tone enhancement unit 37b is arranged between the imaging signal acquisition unit 31 and the dividing processing unit 32. In other words, the color tone enhancement unit 37b according to the first modification of the first and the second embodiments performs an enhancement process on the imaging signal $S_A$ such that a mucosa color distributed in a narrow red region is distributed in a wider region, and outputs an imaging signal $S_K$ subjected to the enhancement process to the dividing processing unit 32.

According to the first modification of the first and the second embodiments of the present disclosure, it is possible to easily recognize a change of color tone between a normal mucosa and an abnormal mucosa.

Second Modification of First and Second Embodiments

Figure 10:
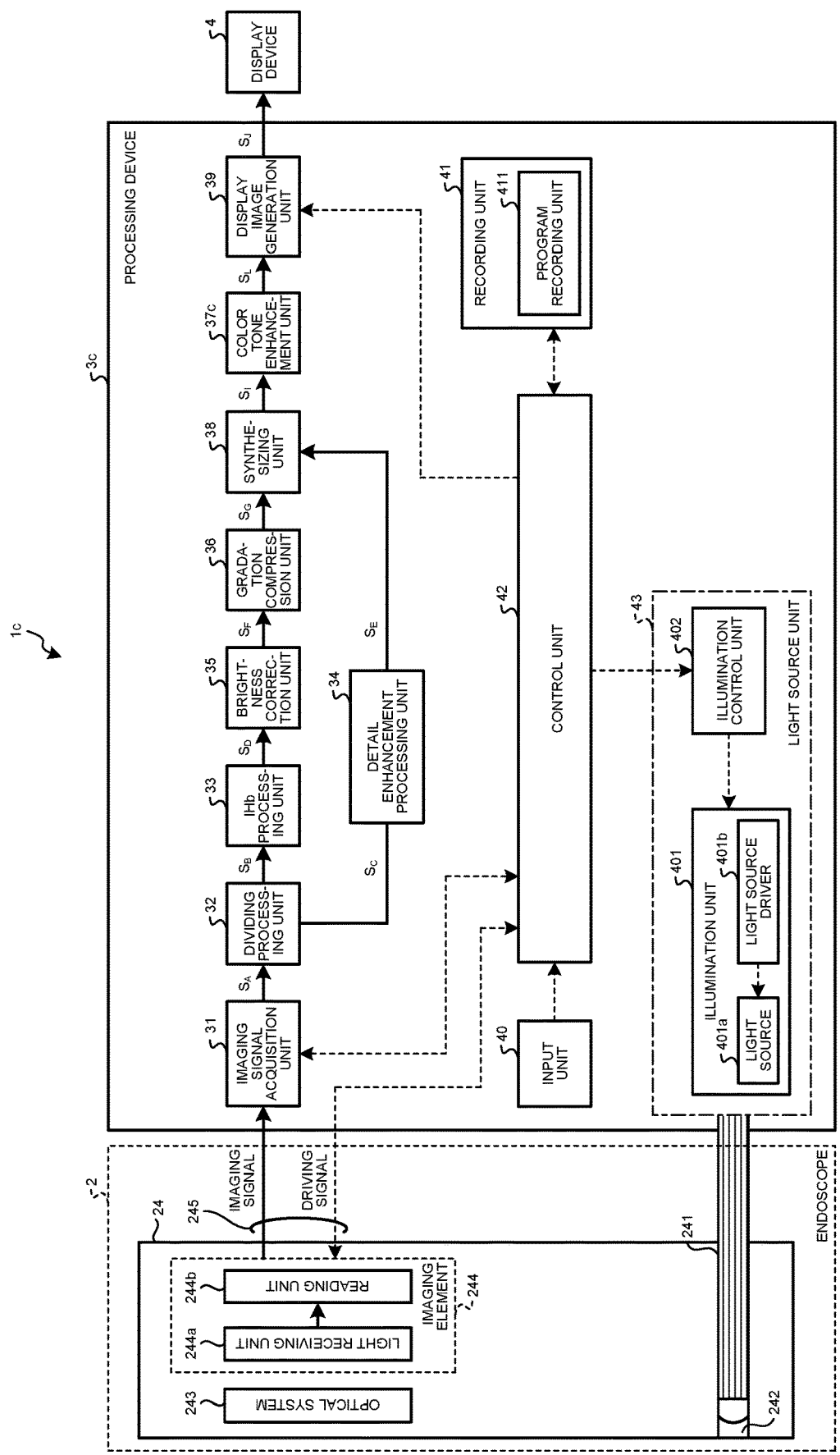
FIG. 10 is a block diagram illustrating a functional configuration of an endoscope system according to a second modification of the first and the second embodiments of the present disclosure.

A second modification of the first and the second embodiments of the present disclosure will be described below. FIG. 10 is a block diagram illustrating a functional configuration of an endoscope system according to the second modification of the first and the second embodiments of the present disclosure.

An endoscope system 1c illustrated in FIG. 10 includes a processing device 3c instead of the processing device 3 of the endoscope system 1 according to the first embodiment as described above. The processing device 3c includes a color tone enhancement unit 37c instead of the color tone enhancement unit 37 of the processing device 3 according to the first embodiment as described above.

The color tone enhancement unit 37c is arranged between the synthesizing unit 38 and the display image generation unit 39. In other words, the color tone enhancement unit 37c according to the second modification of the first and the second embodiments performs an enhancement process on the synthesized signal $S_I$ input from the synthesizing unit 38 such that a mucosa color distributed in a narrow red region is distributed in a wider region, and outputs a synthesized signal $S_L$ subjected to the enhancement process to the display image generation unit 39.

According to the second modification of the first and the second embodiments of the present disclosure, it is possible to easily recognize a change of color tone between a normal mucosa and an abnormal mucosa.

Other Embodiments

Various embodiments may be made by appropriately combining a plurality of structural elements disclosed in the first and the second embodiments of the present disclosure as described above. For example, some structural elements may be deleted from all of the structural elements described in the first and the second embodiments of the present disclosure as described above. Furthermore, the structural elements described in the first and the second embodiments of the present disclosure as described above may be appropriately combined.

Moreover, while the control device and the light source device are integrated in the first and the second embodiments of the present disclosure, the control device and the light source device may be separated from each other.

Furthermore, while the endoscope system has been adopted in the first and the second embodiments of the present disclosure, it is possible to adopt, for example, a capsule endoscope, a video microscope that captures an image of a subject, a mobile phone that has an imaging function, and a tablet terminal that has an imaging function.

Moreover, while the endoscope system including a flexible endoscope has been adopted in the first and the second embodiments of the present disclosure, it may be possible to adopt an endoscope system including a rigid endoscope and an endoscope system including an industrial endoscope.

Furthermore, while the endoscope system including the endoscope that is inserted into a subject is adopted in the first and the second embodiments of the present disclosure, it may be possible to adopt a nasal endoscope and an endoscope system, such as an electric scalpel or an inspection probe.

Moreover, in the first and the second embodiments, a "unit" described above may be replaced with a "means" or a "circuit". For example, the control unit may be replaced with a control means or a control circuit.

Furthermore, a program to be executed by the endoscope system according to the first and the second embodiments of the present disclosure is provided by being recorded in a computer-readable recording medium, such as a compact disc (CD)-ROM, a flexible disk (FD), a CD-recordable (CD-R), a digital versatile disk (DVD), a universal serial bus (USB) medium, or a flash memory, as file data in an installable format or an executable format.

Moreover, the program to be executed by the endoscope system according to the first and the second embodiments of the present disclosure may be configured such that the program is stored in a computer connected to a network, such as the Internet, and provided by downloading via the network. In addition, the program to be executed by the endoscope system according to the first and the second embodiments of the present disclosure may be configured such that the program is provided or distributed via a network, such as the Internet.

Furthermore, in the first and the second embodiments of the present disclosure, a signal is transmitted from an endoscope camera head to the control device via a transmission cable, but transmission need not always be performed in a wired manner and may be performed in a wireless manner. In this case, it is sufficient to transmit an image signal or the like from the endoscope camera head to the control device in accordance with a predetermined radio communication standard (for example, Wi-Fi (registered trademark) or Bluetooth (registered trademark)). It is of course possible to perform radio communication in accordance with other radio communication standard.

In the description of the flowcharts in the present specification, the context of the processes among the steps is clearly indicated using expressions such as "first", "thereafter", and "subsequently", but the order of the processes necessary for carrying out the present disclosure are not uniquely defined by these expressions. In other words, the order of the processes in the flowcharts described in the present specification may be modified as long as there is no contradiction. Furthermore, the disclosure is not limited to such a program including a simple branching process, and a larger number of items may be comprehensively determined to be branched. In this case, a technique of artificial intelligence such as machine learning in prompting the user to perform manual operation and repeating learning may be used together. Moreover, operation patterns performed by many experts may be learned, and deep learning may be performed by incorporating more complicated conditions.

According to the present disclosure, it is possible to easily recognize a change of color tone between a normal mucosa and an abnormal mucosa.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
   a dividing processing circuit configured to divide an imaging signal that is obtained by capturing an image of inside of a subject into a first base component and a detail component, the first base component corresponding to an illumination component of an object, the detail component corresponding to a reflectance component of the object;
   a color enhancement processing circuit configured to generate a second base component by performing a color enhancement process on the first base component, the color enhancement process being a process of increasing color gradation of a mucosa color in a predetermined color space; and
   a synthesizing circuit configured to synthesize the second base component and the detail component to output a synthesized signal, wherein
   the color enhancement processing circuit is configured to
      convert the first base component including an R component, a G component, and a B component into an L component, an a component, and a b component in an Lab color space,
      perform an enhancement process on the a component for extending a color distribution range,
      perform an enhancement process on the b component for extending a color distribution range, and
      convert the a component subjected to the enhancement process, the b component subjected to the enhancement process, and the L component into the second base component including an R component, a G component, and a B component.

2. The image processing apparatus according to claim 1, wherein the color enhancement processing circuit is configured to
   perform an enhancement process on the a component for extending a mucosa color distribution range, and
   perform an enhancement process on the b component for extending a mucosa color distribution range.

3. The image processing apparatus according to claim 1, wherein, the color enhancement processing circuit is configured to
   perform an enhancement process on the a component of the first base component by using a predetermined function, and
   perform an enhancement process on the b component of the first base component based on a value that is standardized by the a component.

4. The image processing apparatus according to claim 1, wherein
   the L component is a brightness component,
   the a component is a red color component, and
   the b component is a blue color component.

5. The image processing apparatus according to claim 1, further comprising:
   a brightness correction circuit configured to perform brightness correction on the base component; and
   a gradation compression circuit configured to perform a gradation compression process on the base component that is subjected to the brightness correction by the brightness correction circuit, wherein
   the color enhancement processing circuit is configured to perform the color enhancement process on the base component that is subjected to the gradation compression process by the gradation compression circuit.

6. An image processing apparatus comprising:
   a dividing processing circuit configured to divide an imaging signal that is obtained by capturing an image of inside of a subject into a base component and a detail component, the base component corresponding to an illumination component of an object, the detail component corresponding to a reflectance component of the object;
   a synthesizing circuit configured to perform a predetermined enhancement process on at least one of the base component and the detail component, and subsequently synthesize the base component and the detail component to output a first synthesized signal; and
   a color enhancement processing circuit configured to output a second synthesized signal that is obtained by performing a color enhancement process on the first synthesized signal output from the synthesizing circuit, the color enhancement process being a process of increasing color gradation of a mucosa color in a predetermined color space, wherein
   the color enhancement processing circuit is configured to
      convert the first synthesized signal including an R component, a G component, and a B component into an L component, an a component, and a b component in an Lab color space,
      perform an enhancement process on the a component for extending a color distribution range,
      perform an enhancement process on the b component for extending a color distribution range, and
      convert the a component subjected to the enhancement process, the b component subjected to the enhancement process, and the L component into the second synthesized signal including an R component, a G component, and a B component.

7. The image processing apparatus according to claim 6, further comprising:
   a brightness correction circuit configured to perform brightness correction on the base component; and
   a gradation compression circuit configured to perform a gradation compression process on the base component that is subjected to the brightness correction by the brightness correction circuit.

8. The image processing apparatus according to claim 6, wherein the color enhancement processing circuit is configured to perform the color enhancement process on at least a blue color component based on a value that is standardized by a red color component.

9. An image processing method comprising:
dividing an imaging signal that is obtained by capturing an image of inside of a subject into a first base component and a detail component, the first base component corresponding to an illumination component of an object, the detail component corresponding to a reflectance component of the object;
generating a second base component by performing a color enhancement process on the first base component, the color enhancement process being a process of increasing color gradation of a mucosa color in a predetermined color space; and
synthesizing the second base component and the detail component to output a synthesized signal, wherein
the color enhancement process includes
converting the first base component including an R component, a G component, and a B component into an L component, an a component, and a b component in an Lab color space,
performing an enhancement process on the a component for extending a color distribution range,
performing an enhancement process on the b component for extending a color distribution range, and
converting the a component subjected to the enhancement process, the b component subjected to the enhancement process, and the L component into the second base component including an R component, a G component, and a B component.

10. An image processing method comprising:
dividing an imaging signal that is obtained by capturing an image of inside of a subject into a base component and a detail component, the base component corresponding to an illumination component of an object, the detail component corresponding to a reflectance component of the object;
performing a predetermined enhancement process on at least one of the base component and the detail component;
after the predetermined enhancement process, synthesizing the base component and the detail component to output a first synthesized signal;
outputting a second synthesized signal that is obtained by performing a color enhancement process on the output first synthesized signal, the color enhancement process being a process of increasing color gradation of a mucosa color on a predetermined color space, wherein
the color enhancement process includes
converting the first synthesized signal including an R component, a G component, and a B component into an L component, an a component, and a b component in an Lab color space,
performing an enhancement process on the a component for extending a color distribution range,
performing an enhancement process on the b component for extending a color distribution range, and
converting the a component subjected to the enhancement process, the b component subjected to the enhancement process, and the L component into the second synthesized signal including an R component, a G component, and a B component.

* * * * *